(12) United States Patent
Park et al.

(10) Patent No.: US 10,179,095 B2
(45) Date of Patent: Jan. 15, 2019

(54) AUTOPHAGE ACTIVATING RESVERATROL TOPICAL COMPOSITION FOR SKIN IMPROVEMENT AND TREATMENT

(71) Applicant: DR. RAYMOND LABORATORIES, Englewood Cliffs, NJ (US)

(72) Inventors: Byeong Deog Park, Bethlehem, PA (US); Chae Hyeong Park, Bethlehem, PA (US)

(73) Assignee: DR. RAYMOND LABORATORIES, Englewood Cliffs, NJ (US)

(*) Notice: Subject to any disclaimer, the term of this patent is extended or adjusted under 35 U.S.C. 154(b) by 0 days.

(21) Appl. No.: 16/002,092

(22) Filed: Jun. 7, 2018

(65) Prior Publication Data

US 2018/0353397 A1    Dec. 13, 2018

Related U.S. Application Data

(60) Provisional application No. 62/516,135, filed on Jun. 7, 2017.

(51) Int. Cl.
| | |
|---|---|
| *A61K 9/127* | (2006.01) |
| *A61K 8/06* | (2006.01) |
| *A61K 9/00* | (2006.01) |
| *A61K 9/107* | (2006.01) |
| *A61K 31/05* | (2006.01) |
| *A61K 31/164* | (2006.01) |

(Continued)

(52) U.S. Cl.
CPC .............. *A61K 8/062* (2013.01); *A61K 8/347* (2013.01); *A61K 8/361* (2013.01); *A61K 8/42* (2013.01); *A61K 8/63* (2013.01); *A61K 9/0014* (2013.01); *A61K 9/107* (2013.01); *A61K 31/05* (2013.01); *A61K 31/164* (2013.01); *A61K 31/20* (2013.01); *A61K 31/57* (2013.01); *A61K 31/575* (2013.01); *A61Q 19/005* (2013.01); *A61Q 19/007* (2013.01)

(58) Field of Classification Search
CPC ....................................................... A61K 9/127
See application file for complete search history.

(56) References Cited

U.S. PATENT DOCUMENTS

| | | | |
|---|---|---|---|
| 2006/0029657 A1* | 2/2006 | Popp .................. | A61K 8/14 424/450 |
| 2008/0057088 A1* | 3/2008 | Blass ................. | A61K 8/0208 424/401 |

(Continued)

FOREIGN PATENT DOCUMENTS

DE    19748399    *  6/1999

OTHER PUBLICATIONS

Vanaja, K., et al in Life Sciences, issue 24, Dec. 2013, pp. 917-923.*

(Continued)

*Primary Examiner* — Gollamudi Kishore
(74) *Attorney, Agent, or Firm* — SIMI Law Group, P.C.

(57) ABSTRACT

An autophage activating resveratrol topical composition includes a ceramide or a pseudoceramide, a fatty acid, a phytosterol, and a resveratrol. The ceramide or pseudoceramide, the fatty acid, the phytosterol, and the resveratrol form a multi-layered encapsulation system. A method of inducing autophagy in skin includes applying the autophage activating resveratrol topical composition to a skin, and inducing autophagy in the skin to improve skin barrier function and skin self-purification function.

11 Claims, 1 Drawing Sheet

(51) Int. Cl.
  *A61K 31/575* (2006.01)
  *A61K 8/63* (2006.01)
  *A61K 31/20* (2006.01)
  *A61Q 19/00* (2006.01)
  *A61K 8/34* (2006.01)
  *A61K 8/42* (2006.01)
  *A61K 8/36* (2006.01)
  *A61K 31/57* (2006.01)

(56) References Cited

U.S. PATENT DOCUMENTS

| | | | | |
|---|---|---|---|---|
| 2009/0017108 A1* | 1/2009 | Yuzhakov | ............ | A61K 9/1271 424/450 |
| 2014/0235690 A1* | 8/2014 | Andrews | ............ | A61K 9/0019 514/412 |
| 2016/0114054 A1* | 4/2016 | Kuebelbeck | ............ | A61K 51/08 514/15.4 |

OTHER PUBLICATIONS

Augustin, M.A., et al in Annals of The New York Academy of Sciences, 1290, pp. 107-112, 2013.*
Caddeo, C., et al in International Journal of Pharmaceutics, vol. 363, issues 1-2, Nov. 2008, pp. 183-191.*
Park, B.D., et al, The Journal of Investigative Dermatology, vol. 121, # 4, Octomber 2003, pp. 794-801.*
Chen Rong-Jane et al in Journal of Food and Drug Analysis, vol. 25, Issue 1, Jan. 2017, pp. 125-133.*
Li . L., et al in Oncotarget, vol. 7, # 31, pp. 50682-50697Min Sik Choi et al in Experimental Dermatology, vol. 22, pp. 491-494, 2013.*
Ziang, W., Biochimica Biophysica Acta, vol. 1841, issue 5, May 2014, pp. 783-792.*

* cited by examiner

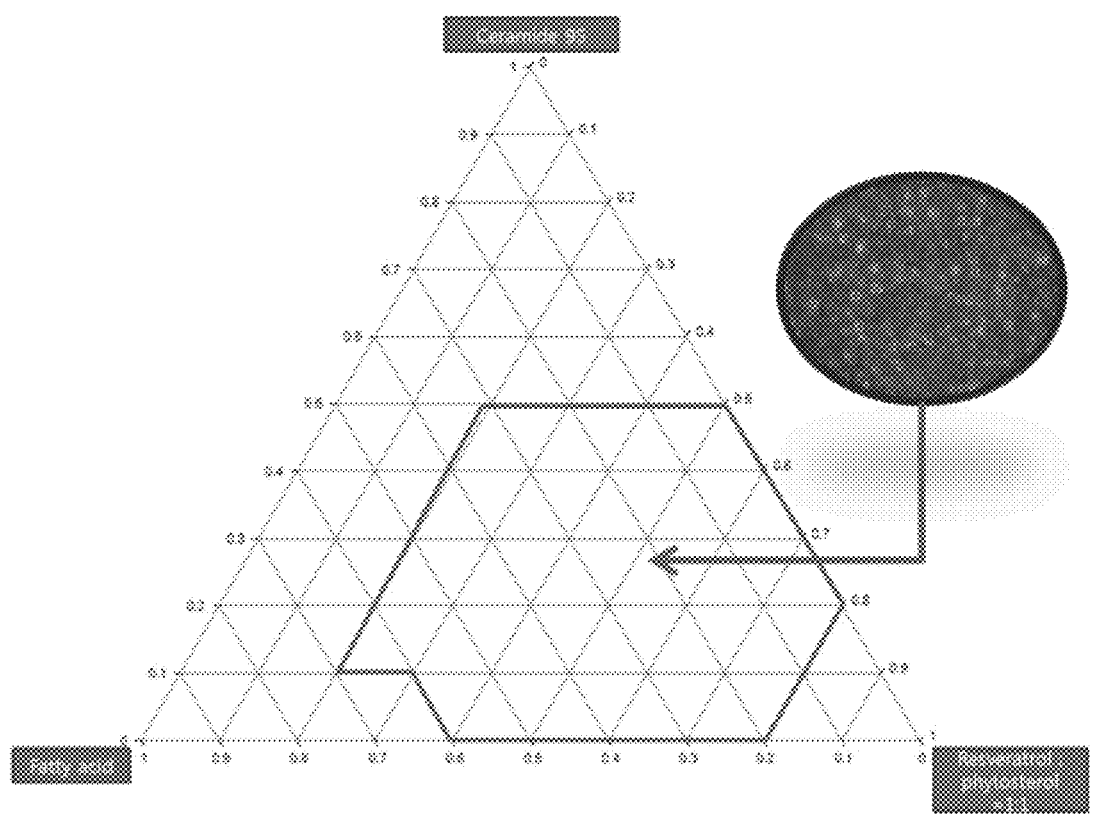

AUTOPHAGE ACTIVATING RESVERATROL TOPICAL COMPOSITION FOR SKIN IMPROVEMENT AND TREATMENT

This application claims priority to U.S. Provisional Patent Application No. 62/516,135, filed Jun. 7, 2018, which is incorporated by reference for all purposes as if fully set forth herein.

FIELD OF THE INVENTION

The present invention relates to a topical composition, specifically, an autophage activating resveratrol topical composition for skin improvement and treatment.

BACKGROUND OF THE INVENTION

The word autophagy originates from the Greek words auto-, meaning "self", and phagein, meaning "to eat." Thus, autophagy denotes "self eating." The 2016 Nobel Prize in Physiology or Medicine was awarded to Yoshinori Ohsumi for his discoveries of mechanisms for autophagy. Autophagy is a fundamental process for degrading and recycling cellular components. During autophagy, damaged, unnecessary, dysfunctional macromolecules and organelles are broken down and are recycled for building new cellular components. In particular, autophagy makes it possible to regulate, repair and eliminate proteins with a long service life in the cells, thus ensuring a control during differentiation and aging of human skin. Autophagy could play a role in skin care.

Resveratrol is well known autophagy activator. Resveratrol readily becomes unstable in an aqueous solution or under exposure to the air. Hence it is important to stabilize the oleophilic ingredients in cosmetics and external preparations for skin improvement and treatment with autophagy function. There are generally two methods to stabilize dermatologically useful oleophilic ingredients: (1) encapsulation method and (2) emulsified formulation method.

As multi layered encapsulation, the mimic system of skin barrier of intact skin has many of advantages such as skin barrier recovery, skin compatibility. The main ingredients of the skin mimic multi layered encapsulation system are based on the skin physiological feature and include, for example, ceramide, pseudoceramide, fatty acid. Cholesterol is the main ingredient in human skin, and is commonly used in the emulsified formulation method to stabilize the oleophilic ingredients. Cholesterol is an animal raw material, and, in recent years, the cosmetics industry is reluctant to use animal raw materials. Cholesterol can also be derived from yeast, but the production cost is high.

There is a need for an autophage activating resveratrol topical composition for skin improvement and treatment to meet industrial demand. The resveratrol topical composition with stable multi layered encapsulation system can induce autophagy. This will be efficacious for skin barrier function and also for skin's self-purification system which benefits sensitive skin and atopic dermatitis patients.

SUMMARY OF THE INVENTION

In one embodiment, the present invention provides an autophage activating resveratrol topical composition. The autophage activating resveratrol topical composition includes a ceramide or a pseudoceramide, a fatty acid, a phytosterol, and a resveratrol. The ceramide or pseudoceramide, the fatty acid, the phytosterol, and the resveratrol form a multi-layered encapsulation system.

The autophage activating resveratrol topical composition may include a ceramide or pseudoceramide. The pseudoceramide is represented by formula (I) or formula (II).

R1-COCHR2CONR3R4 (I)

R1-CH(OH)CHR2CONR3R4 (II)

In formulas (I) and (II), R1 and R2 are independently linear or branched C6-C22 alkyl group or C6-C22 alkenyl group, R3 and R4 are independently hydrogen, methyl, ethyl, propyl, or linear or branched C2-C6 alkyl group having one or more hydroxyl groups, or monosaccharide with the proviso that when either R3 or R4 is hydrogen, the other is not hydroxyethyl.

In another embodiment, the pseudoceramide is represented by formula (I), $R_1$ is —$C_{15}H_{31}$ or —$C_{17}H_{35}$, $R_2$ is —$C_{14}H_{29}$ or —$C_{16}H_{33}$, $R_3$ is H and $R_4$ is —$CH_2CH_2OH$, and the pseudoceramide is ceramide 9S.

In another embodiment, the pseudoceramide is represented by formula (II), $R_1$ is —$C_{15}H_{31}$ or —$C_{17}H_{35}$ and $R_2$ is —$C_{14}H_{29}$ or —$C_{16}H_{33}$, $R_3$ is H and $R_4$ is —$CH(CH_2OH)_2$, and the pseudoceramide is ceramide 5P.

In another embodiment, the pseudoceramide is ceramide IIIB.

In another embodiment, the fatty acid is a saturated or unsaturated carboxylic acid with a long aliphatic chain.

In another embodiment, the phytosterol is selected from the group consisting of β-sitosterol, campesterol, cholesterol, stigmasterol, stigmastanol, campestanol, brassicasterol, ergosterol, lupeol, and cycloartenol.

In another embodiment, the resveratrol is represented by the following structure:

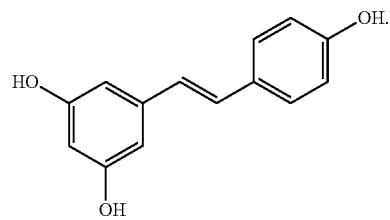 [SMILES: Oc1ccc(/C=C/c2cc(O)cc(O)c2)cc1]

In another embodiment, the pseudoceramide is in an amount of less than 20% of a total weight of the resveratrol topical composition.

In another embodiment, the fatty acid is in an amount of less than 70% of the total weight of the resveratrol topical composition.

In another embodiment, a weight ratio of the phytosterol and the resveratrol is between 1:9 to 9:1.

In another embodiment, the weight ratio of the phytosterol and the resveratrol is 1:1.

In another embodiment, the autophage activating resveratrol topical composition further includes emulsifier oils and cosmetic ingredients.

In another embodiment, the autophage activating resveratrol topical composition includes 0.5-1.0 wt % of the ceramide or pseudoceramide, 1.0-7.0 wt % of the fatty acid, 0.01-1.0 wt % of the phytosterol, and 0.01-1.0 wt % of the resveratrol.

In one embodiment, the present invention provides an autophage activating resveratrol topical composition. The autophage activating resveratrol topical composition consists of a ceramide or pseudoceramide, a fatty acid, a phytosterol, and a resveratrol. The ceramide or pseudoceramide, the fatty acid, the phytosterol, and the resveratrol form a multi-layered encapsulation system.

In another embodiment, the pseudoceramide is ceramide 9S.

In another embodiment, the pseudoceramide is ceramide 5P.

In another embodiment, the pseudoceramide is ceramide IIIB.

In another embodiment, the fatty acid is a saturated or unsaturated carboxylic acid with a long aliphatic chain.

In another embodiment, the phytosterol is selected from the group consisting of β-sitosterol, campesterol, cholesterol, stigmasterol, stigmastanol, campestanol, brassicasterol, ergosterol, lupeol, and cycloartenol.

In another embodiment, the resveratrol is represented by the following structure:

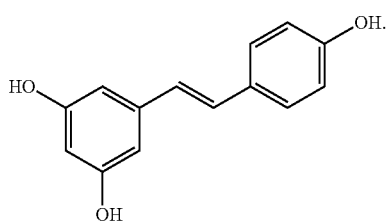 [SMILES: Oc1ccc(/C=C/c2cc(O)cc(O)c2)cc1]

In one embodiment, the present invention provides a method of inducing autophagy in skin. The method includes applying the autophage activating resveratrol topical composition to a skin, and inducing autophagy in the skin to improve skin barrier function and skin self-purification function.

In another embodiment, the skin is a sensitive skin or atopic dermatitis skin.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows a three-phase diagram study of ceramide 9S, fatty acid and a 1:1 mixture of phytosterol and resveratrol.

DETAILED DESCRIPTION OF THE ILLUSTRATED EMBODIMENTS

Reference will now be made in detail to embodiments of the present invention, example of which is illustrated in the accompanying drawings.

The present invention provides an autophage activating resveratrol topical composition that includes a ceramide or pseudoceramide, a fatty acid, a phytosterol, and a resveratrol. The ceramide (or pseudoceramide), the fatty acid, the phytosterol, and the resveratrol may form a multi-layered encapsulation system.

Ceramides are prominent lipids found in stratum corneum, the outermost layer of epidermis, and has an important function in formation and retention of stratum corneum. Pseudoceramides have similar structures to natural ceramides. Skin damage caused by detergents which remove the lipids essential for the barrier function will result in an increased transdermal water loss (TEWL), and deteriorated barrier function has negative consequences for the total condition of the skin. A damaged skin barrier leads to increased skin sensitivity and potential irritation such as atopic dermatitis or psoriasis. Topical applications of ceramide or pseudoceramide containing compositions are effective in relieving atopic eczema. Ceramide or pseudoceramide also exhibit therapeutic properties such as wound and ulcer healing through the promotion of cell restoration and growth.

The autophage activating resveratrol topical composition may include a ceramide or pseudoceramide. The pseudoceramide is represented by formula (I) or formula (II).

$$R_1-COCHR_2CONR_3R_4 \quad (I)$$

$$R_1-CH(OH)CHR_2CONR_3R_4 \quad (II)$$

In formulas (I) and (II), $R_1$ and $R_2$ are independently linear or branched $C_6$-$C_{22}$ alkyl group or $C_6$-$C_{22}$ alkenyl group, $R_3$ and $R_4$ are independently hydrogen, methyl, ethyl, propyl, or linear or branched $C_2$-$C_6$ alkyl group having one or more hydroxyl groups, or monosaccharide with the proviso that when either $R_3$ or $R_4$ is hydrogen, the other is not hydroxyethyl.

In formula (I), $R_1$ can be $-C_{15}H_{31}$ or $-C_{17}H_{35}$ and $R_2$ can be $-C_{14}H_{29}$ or $-C_{16}H_{33}$. R3 is H and R4 is $-CH_2CH_2OH$. In this case, the pseudoceramide is ceramide 9S.

In formula (II), $R_1$ can be $-C_{15}H_{31}$ or $-C_{17}H_{35}$ and $R_2$ can be $-C_{14}H_{29}$ or $-C_{16}H_{33}$, R3 is H and R4 is $-CH(CH_2OH)_2$. In this case, the pseudoceramide is ceramide 5P.

The resveratrol topical composition may include a fatty acid. The fatty acid is a saturated or unsaturated carboxylic acid with a long aliphatic chain (from 4 to 28 carbon atoms).

The resveratrol topical composition may include a phytosterol. Phytosterols include plant sterols and stanols and are phytosteroids which occur in plants and vary only in carbon side chains and/or presence or absence of a double bond. Stanols are saturated sterols, having no double bonds in the sterol ring structure. Examples of phytosterols include, but not limited to, β-sitosterol, campesterol, cholesterol, stigmasterol, stigmastanol, campestanol, brassicasterol, ergosterol, lupeol, and cycloartenol.

β-sitosterol
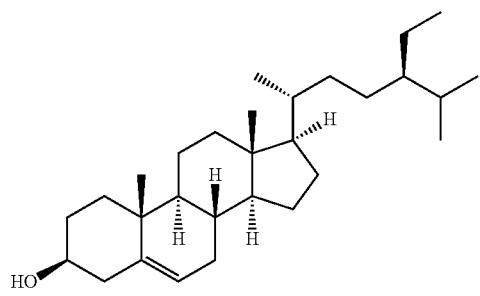
campesterol
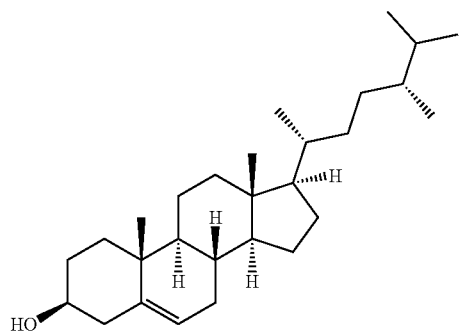
cholesterol
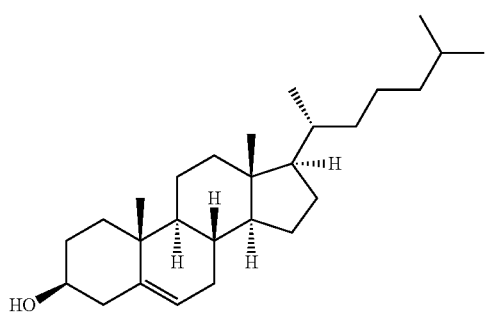
stigmasterol
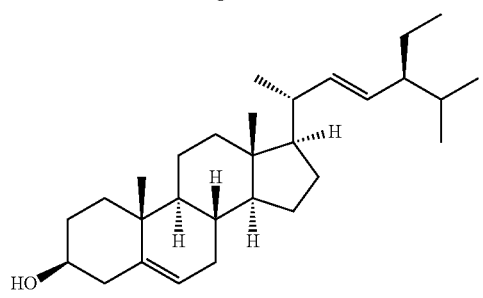
stigmastanol
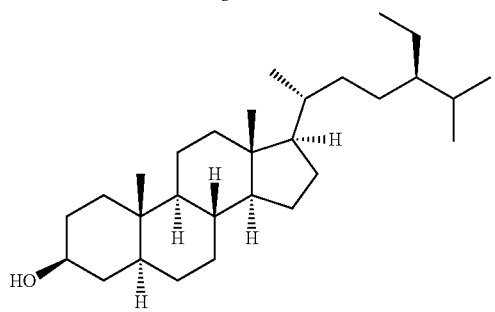
campestanol
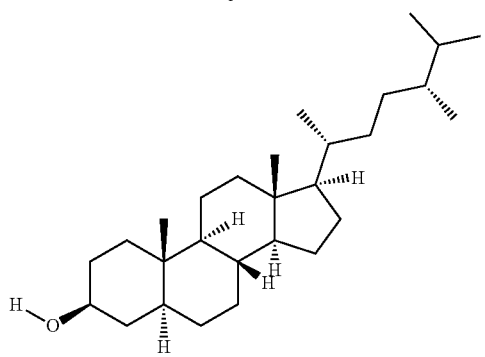
brassicasterol
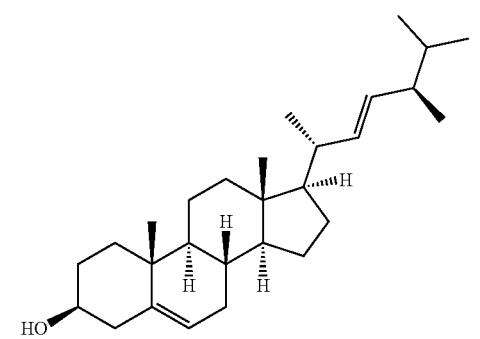
ergosterol
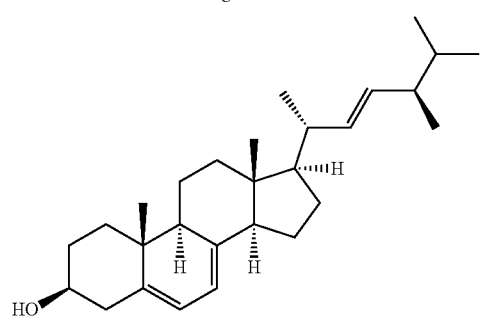
lupeol
cycloartenol -continued

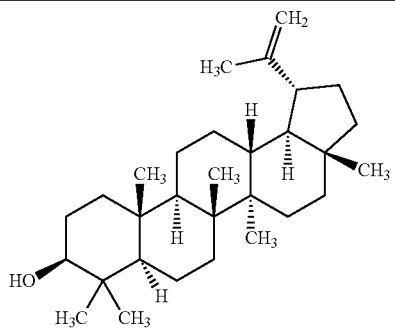
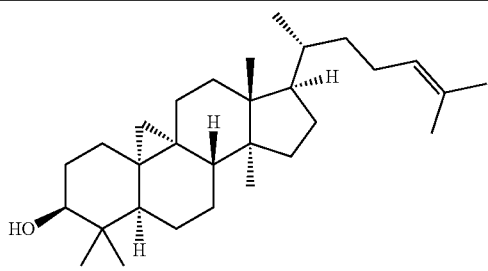

The resveratrol topical composition may include a resveratrol. Resveratrol is a natural phenol and produced by several plants. Resveratrol has the following the structure.

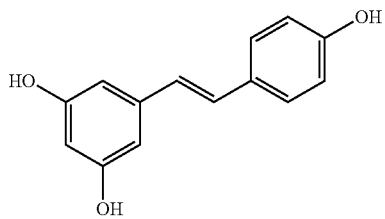 [SMILES: Oc1ccc(/C=C/c2cc(O)cc(O)c2)cc1]

The pseudoceramide, the fatty acid, the phytosterol, and the resveratrol may form a multi-layered encapsulation system (MLE), which is an oil-in-water (O/W) emulsion showing multi-lamella structure. In a multi-layered encapsulation system, lamellar structure is observed in stratum corneum (a thin plate or membrane of skin lipids). Multi-layered encapsulation system shows a multiple-layer structure. The multi-layered encapsulation system can be used as a moisturizer, offering long-lasting skin moisturizing effects through reinforcing the skin's natural barrier function.

To decide optimum ratio between, ceramide, fatty acid, resveratrol, and phytosterol, a three-phase diagram study was conducted. The three-phase diagram study is shown in FIG. 1. FIG. 1 shows the area where the lamellar liquid crystal structure appears in the three-phase boundary.

Specifically, as shown in FIG. 1, the resveratrol topical composition may include a pseudoceramide in an amount of less than 20% of a total weight of the resveratrol topical composition. The optimum ratio to make lamella encapsulation system in 3 phase diagram is: Ceramide 9S: 0%-50% (0-0.5); Fatty acid: 0%-70% (0-0.7); Resveratrol/phytosterol mixture (1:1): 20%-80% (0.2-0.8); Total: 100% (total is 1.0).

The resveratrol topical composition may include a fatty acid is in an amount of less than 30% of the total weight of the resveratrol topical composition. It is possible to use a large amount of fatty acid because the fatty acid forms an anti-microbial barrier and helps to form multi-layered encapsulation system. Given the effects of pseudoceramide, phytosterol and resveratrol, it is desirable not to exceed a maximum of 30%.

In the resveratrol topical composition, a weight ratio of the phytosterol and the resveratrol may be between 1:9 to 9:1. Preferably, the weight ratio of the phytosterol and the resveratrol is 1:1. The ratio of the phytosterol and the resveratrol may effect the formation of the multi-layered encapsulation system.

The resveratrol topical composition may further include emulsifier oils and cosmetic ingredients.

The resveratrol topical composition may include 0.5-1.0 wt % of the pseudoceramide, 1.0-7.0 wt % of the fatty acid, 0.01-1.0 wt % of the phytosterol, and 0.01-1.0 wt % of the resveratrol.

The present invention will be described in detail by way of the following examples and experimental examples, which are not intended to limit the scope of the present invention.

Examples 1-5

Ceramide 9S and Ceramide 5P and Ceramide TIM, fatty acid, cholesterol, phytosterol, resveratrol, triglyceride, glycerin, 1,3-butylene glycol, cetanol, glycerylmonostearate, POE(15)glycerylmonostearate, carbomer, and purified water were mixed to prepare multi-lamella emulsion.

TABLE 1

| | Examples 1-5 | | | | |
| --- | --- | --- | --- | --- | --- |
| wt% | Example 1 | Example 2 | Example 3 | Example 4 | Example 5 |
| Ceramide 9S | 0.6 | 0.6 | 0.6 | | 0.5 |
| Ceramide 5P | | | | 0.6 | |
| Ceramide IIIB | | | | | 0.1 |
| fatty acid | 1.5 | 1.5 | 1.5 | 1.5 | 1.5 |
| cholesterol | 0.2 | | | | |
| phytosterol | | 0.15 | 0.1 | 0.1 | 0.1 |
| resveratrol | | 0.05 | 0.1 | 0.1 | 0.1 |
| triglyceride | 5.5 | 5.5 | 5.5 | 5.5 | 5.5 |
| glycerin | 5.0 | 5.0 | 5.0 | 5.0 | 5.0 |
| 1,3-butylene glycol | 5.0 | 5.0 | 5.0 | 5.0 | 5.0 |
| cetanol | 3.5 | 3.5 | 3.5 | 3.5 | 3.5 |
| glyceryl-monostearate | 1.5 | 1.5 | 1.5 | 1.5 | 1.5 |
| POE(15)glyceryl monostearate | 3.5 | 3.5 | 3.5 | 3.5 | 3.5 |
| carbomer | 0.2 | 0.2 | 0.2 | 0.2 | 0.2 |
| water | 74.0 | 74.0 | 74.0 | 74.0 | 74.0 |

Ceramide IIIB has the following structure:

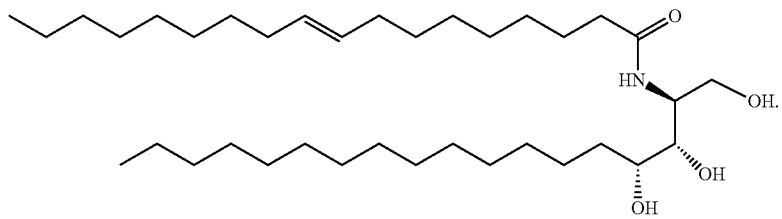 [SMILES: CCCCCCCC/C=C/CCCCCCCC(=O)N[C@@H](CO)[C@H](O)[C@H](O)CCCCCCCCCCCCCC]

Examples 1-5 were tested for barrier recovery. Examples 1-5 were applied to dry and barrier-impaired skin, such as atopic eczema, twice a day for two weeks. Transepidermal water loss (TEWL) measurements were performed after one and two weeks with a Tewameter TM210 (C+K electronic, Germany). TEWL measures the quantity of water that passes from inside a body through the epidermal layer (skin) to the surrounding atmosphere via diffusion and evaporation processes. The measurements were presented as percent of TEWL measurement of normal skin.

TABLE 2

| Barrier Recovery (%) | Example 1 | Example 2 | Example 3 | Example 4 | Example 5 |
|---|---|---|---|---|---|
| One week | 85.4 | 86.6 | 87.4 | 88.5 | 87.5 |
| Two weeks | 99.4 | 99.5 | 99.5 | 99.5 | 99.5 |

Compared to cholesterol-based topical composition (Example 1), the combination of phytosterol and resveratrol (Examples 2-5) show superior skin recovery when applied to dry and barrier-impaired skin.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An autophage activating resveratrol topical composition comprising:
   0.5-1.0 wt % of a pseudoceramide,
   1.0-7.0 wt % of a fatty acid,
   0.01-1.0 wt % of a phytosterol, and
   0.01-1.0 wt % of a resveratrol,
   wherein the ceramide or pseudoceramide, the fatty acid, the phytosterol, and the resveratrol form a multi-layered encapsulation system, and
   wherein the pseudoceramide is ceramide 9S, ceramide 5P, or ceramide IIIB.

2. The autophage activating resveratrol topical composition of claim 1, wherein the fatty acid is a saturated or unsaturated carboxylic acid with a long aliphatic chain.

3. The autophage activating resveratrol topical composition of claim 1, wherein the phytosterol is selected from the group consisting of β-sitosterol, campesterol, cholesterol, stigmasterol, stigmastanol, campestanol, brassicasterol, ergosterol, lupeol, and cycloartenol.

4. The autophage activating resveratrol topical composition of claim 1, wherein the resveratrol is represented by the following structure:

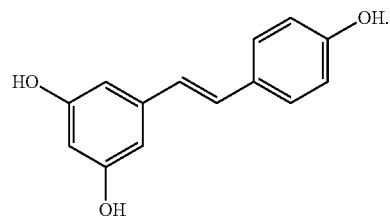 [SMILES: Oc1ccc(/C=C/c2cc(O)cc(O)c2)cc1]

5. The autophage activating resveratrol topical composition of claim 1, wherein the pseudoceramide is in an amount of less than 20% of a total weight of the resveratrol topical composition.

6. The autophage activating resveratrol topical composition of claim 1, wherein the fatty acid is in an amount of less than 70% of the total weight of the resveratrol topical composition.

7. The autophage activating resveratrol topical composition of claim 1, wherein a weight ratio of the phytosterol and the resveratrol is between 1:9 to 9:1.

8. The autophage activating resveratrol topical composition of claim 7, wherein the weight ratio of the phytosterol and the resveratrol is 1:1.

9. The autophage activating resveratrol topical composition of claim 1 further comprising:
   emulsifier oils and cosmetic ingredients.

10. A method of inducing autophagy in skin comprising:
    applying the autophage activating resveratrol topical composition of claim 1 to a skin, and
    inducing autophagy in the skin to improve skin barrier function and skin self-purification function.

11. The method of claim 10, wherein the skin is a sensitive skin or atopic dermatitis skin.

* * * * *